US011598947B2

(12) United States Patent
Watanabe et al.

(10) Patent No.: US 11,598,947 B2
(45) Date of Patent: Mar. 7, 2023

(54) RELAY OPTICAL SYSTEM FOR RIGID ENDOSCOPE

(71) Applicants: Sumita Optical Glass, Inc., Saitama (JP); Dayong Li, Saitama (JP)

(72) Inventors: Hiroki Watanabe, Saitama (JP); Morito Kanke, Saitama (JP); Shotaro Sano, Saitama (JP); Jun Otake, Saitama (JP); Dayong Li, Saitama (JP)

(73) Assignees: Sumita Optical Glass, Inc., Saitama (JP); Dayong Li, Saitama (JP)

( * ) Notice: Subject to any disclaimer, the term of this patent is extended or adjusted under 35 U.S.C. 154(b) by 120 days.

(21) Appl. No.: 17/268,085

(22) PCT Filed: Jul. 10, 2019

(86) PCT No.: PCT/JP2019/027408
§ 371 (c)(1),
(2) Date: Feb. 12, 2021

(87) PCT Pub. No.: WO2020/044807
PCT Pub. Date: Mar. 5, 2020

(65) Prior Publication Data
US 2021/0349304 A1   Nov. 11, 2021

(30) Foreign Application Priority Data

Aug. 28, 2018  (JP) .............................. JP2018-159686

(51) Int. Cl.
*G02B 23/24*    (2006.01)
*G02B 7/02*     (2021.01)

(52) U.S. Cl.
CPC ......... *G02B 23/2446* (2013.01); *G02B 7/028* (2013.01); *G02B 23/243* (2013.01); *G02B 23/2461* (2013.01)

(58) Field of Classification Search
CPC .. G02B 23/2446; G02B 7/028; G02B 23/243; G02B 23/2461; G02B 7/02; G02B 7/021;
(Continued)

(56) References Cited

U.S. PATENT DOCUMENTS 5,188,092 A    2/1993   White

FOREIGN PATENT DOCUMENTS

JP     S495993 B1    2/1974
JP     H07134246 A   5/1995
(Continued)

OTHER PUBLICATIONS

Mar. 2, 2021, International Preliminary Report on Patentability issued in the International Patent Application No. PCT/JP2019/027408.
(Continued)

*Primary Examiner* — Arnel C Lavarias
(74) *Attorney, Agent, or Firm* — Kenja IP Law PC (57) ABSTRACT

A relay optical system 20 for a rigid endoscope includes a lens fixing frame 21 and a plurality of lenses 22. The lens fixing frame 21 has a plurality of tubular bodies 26. The plurality of tubular bodies 26 are joined coaxially to each other. The plurality of lenses 22 are located at positions other than a joint position jp of the tubular bodies 26 in an axis direction of the lens fixing frame 21. The plurality of lenses 22 are located in the lens fixing frame 21 so as to have a coincident optical axis. The plurality of lenses 22 do not include a cemented lens.

5 Claims, 4 Drawing Sheets

(58) Field of Classification Search
CPC ........ G02B 7/025; G02B 7/026; G02B 23/00; G02B 23/16; G02B 23/24; G02B 23/2407; G02B 23/2476; G02B 23/2492; A61B 1/00; A61B 1/0002; A61B 1/00064; A61B 1/00071; A61B 1/00096; A61B 1/00105; A61B 1/00112; A61B 1/00119; A61B 1/00163; A61B 1/002; A61B 1/06
USPC ............... 359/434, 362, 363, 368, 369, 435; 600/101, 128, 129, 130, 133, 136, 138, 600/160, 181
See application file for complete search history.

(56) References Cited

FOREIGN PATENT DOCUMENTS

| | | | | | |
|---|---|---|---|---|---|
| JP | 08122667 | A | * | 5/1996 | ............. A61B 1/002 |
| JP | 2000162508 | A | | 6/2000 | |
| JP | 2002131509 | A | | 5/2002 | |
| JP | 2002365510 | A | | 12/2002 | |
| JP | 2007330706 | A | | 12/2007 | |
| JP | 2010158412 | A | | 7/2010 | |
| JP | 2015118136 | A | | 6/2015 | |
| JP | 2017074267 | A | * | 4/2017 | |
| JP | 2017221658 | A | * | 12/2017 | |
| JP | 2017221658 | A | | 12/2017 | |
| JP | 2017223806 | A | | 12/2017 | |
| WO | WO-2018135192 | A1 | * | 7/2018 | ............... A61B 1/00 |

OTHER PUBLICATIONS

Jun. 7, 2022, Notification of Reasons for Refusal issued by the Japan Patent Office in the corresponding Japanese Patent Application No. 2018-159686.

May 7, 2022, Office Action issued by the China National Intellectual Property Administration in the corresponding Chinese Patent Application No. 201980052742.X.

Sep. 3, 2019, International Search Report issued in the International Patent Application No. PCT/JP2019/027408.

Jan. 9, 2023, Office Action issued by the China National Intellectual Property Adminstration in the corresponding Chinese Patent Application No. 201980052742.X.

* cited by examiner

RELAY OPTICAL SYSTEM FOR RIGID ENDOSCOPE

CROSS REFERENCE TO RELATED APPLICATION

This application claims priority to Japanese Patent Application No. 2018-159686 filed on Aug. 28, 2018, the entire disclosure of which is incorporated herein by reference.

TECHNICAL FIELD

The present disclosure relates to a relay optical system for a rigid endoscope.

BACKGROUND

Rigid endoscopes are used in the fields of medicine, industry, and the like. A rigid endoscope uses many lenses to transfer a subject image at the distal end of an insertion portion to the proximal side. For good visibility of the subject image, the multiple lenses are required to be fixed in a state of being aligned in the optical axis direction with high accuracy. Conventionally, a cemented lens (see JP 2015-118136 A (PTL 1)), a lens pressing tube (see JP 2010-158412 A (PTL 2)), and the like are used for fixing in high-accuracy alignment.

CITATION LIST

Patent Literature

PTL 1: JP 2015-118136 A
PTL 2: JP 2010-158412 A

SUMMARY

Technical Problem

Rigid endoscopes used in the fields such as medicine need to be sterilized upon each use. Conventional rigid endoscopes are sterilized by a Sterrad sterilization method. However, given that a device for performing the Sterrad sterilization method is expensive, the use of an autoclave sterilization method which is low in cost is desired. With the autoclave sterilization method, a rigid endoscope is exposed to high temperature and high pressure. At high temperature and high pressure, there is a possibility that lenses in the rigid endoscope are displaced and misaligned due to contraction or the like and the initial optical property decreases.

It could therefore be helpful to provide a relay optical system for a rigid endoscope that can maintain optical property within tolerance even when exposed to high temperature and high pressure.

Solution to Problem

A relay optical system for a rigid endoscope according to a first aspect comprises: a lens fixing frame having a plurality of tubular bodies that are joined coaxially to each other; and a plurality of lenses located in the lens fixing frame so as to have a coincident optical axis, at positions other than a joint position of the tubular bodies in an axis direction of the lens fixing frame, the plurality of lenses not including a cemented lens.

Preferably, in a relay optical system for a rigid endoscope according to a second aspect, at least one of the plurality of tubular bodies has, as part of the plurality of lenses, a front lens group including a lens having positive refractive power and a lens having negative refractive power in proximity to each other, a rear lens group including a lens having negative refractive power and a lens having positive refractive power in proximity to each other, and a middle lens located between the front lens group and the rear lens group and having positive refractive power.

Preferably, in a relay optical system for a rigid endoscope according to a third aspect, in at least one of the front lens group and the rear lens group, the lens having positive refractive power and the lens having negative refractive power are butted against each other outside an effective diameter thereof.

Preferably, a relay optical system for a rigid endoscope according to a fourth aspect further comprises an aperture stop for the plurality of lenses, the aperture stop being located near the joint position of the tubular bodies.

Preferably a relay optical system for a rigid endoscope according to a fifth aspect further comprises an adhesive body extending from a through hole formed in each of at least three locations along a circumferential direction of the lens fixing frame to an outer edge of at least part of the plurality of lenses, and fixing the at least part of the plurality of lenses to the lens fixing frame.

Preferably, in a relay optical system for a rigid endoscope according to a sixth aspect, a glass transition temperature of the adhesive body is higher than or equal to a sterilization treatment temperature.

Preferably, in a relay optical system for a rigid endoscope according to a seventh aspect, $Ec \geq (El+Es)$, where $Ec$ is a thermal expansion coefficient of the lens fixing frame, $El$ is a thermal expansion coefficient of each of the plurality of lenses, and $Es$ is a thermal expansion coefficient of a gap ring that adjusts a position of at least part of the plurality of lenses in an optical axis direction.

Advantageous Effect

According to the present disclosure, optical property can be maintained within tolerance even when exposed to high temperature and high pressure.

DETAILED DESCRIPTION

One of the disclosed embodiments will be described below, with reference to the drawings.

Figure 1:
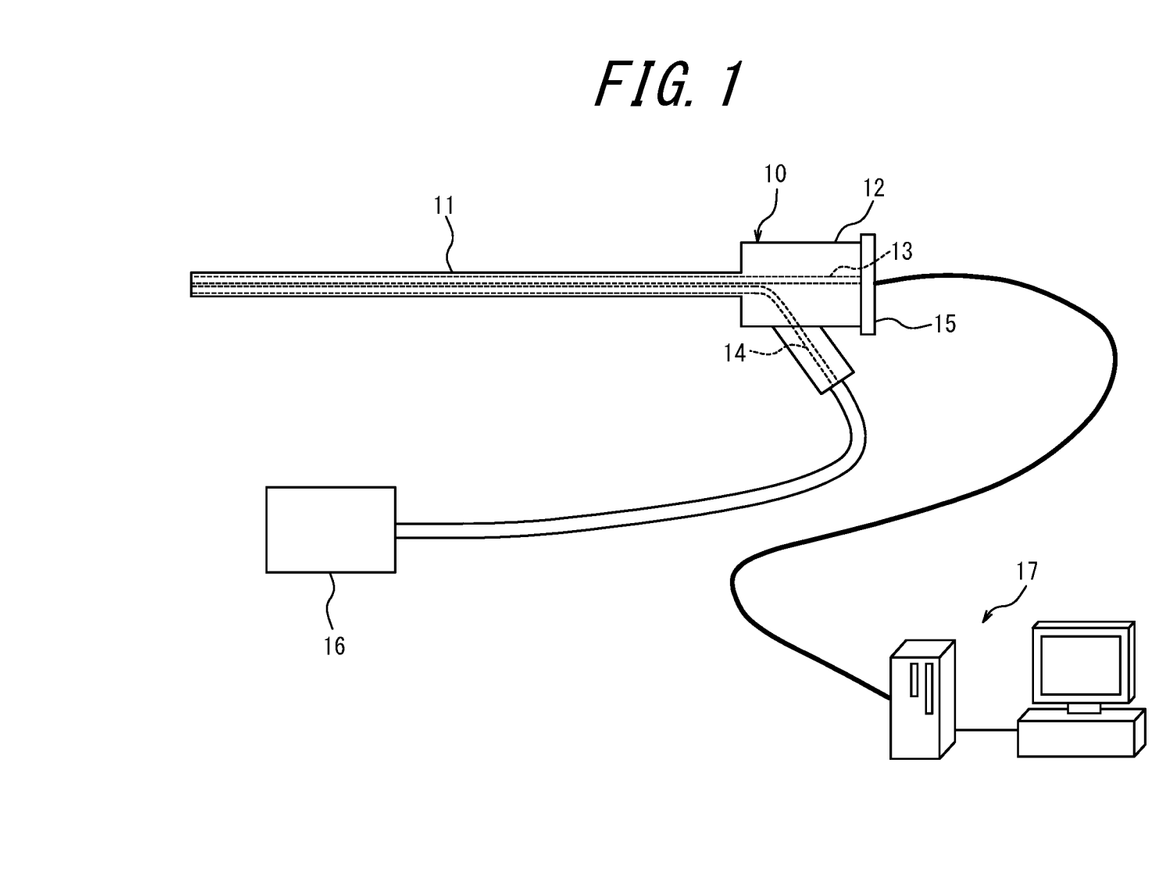
FIG. 1 is an external diagram schematically illustrating a structure of a rigid endoscope including a relay optical system according to one of the disclosed embodiments.

FIG. 1 is a schematic diagram of a rigid endoscope 10 using a relay optical system 20 for a rigid endoscope according to one of the disclosed embodiments. The rigid endoscope 10 includes an insertion portion 11 and an operation portion 12.

The insertion portion 11 is a rigid cylinder. For example, the insertion portion 11 is inserted into the body or the like from the distal side and used. The operation portion 12 is connected to the proximal side of the insertion portion 11. The operation portion 12 can be held by a user in order to adjust the insertion position of the insertion portion 11 and the like.

The insertion portion 11 is provided with a rigid endoscope optical system 13 and a light guide 14 that extend over the proximal end from the distal end. The rigid endoscope optical system 13 extends into the operation portion 12. The rigid endoscope optical system 13 can be optically coupled to a camera 15 attached to the operation portion 12, on the operation portion 12 side. The camera 15 is removable from the operation portion 12. The light guide 14 passes through the operation portion 12 and extends to the outside of the rigid endoscope 10. The end of the light guide 14 extending from the operation portion 12 side can be removably connected to a light source device 16.

When using the rigid endoscope 10, illumination light emitted from the light source device 16 is applied to an observation object near the distal end of the insertion portion 11, via the light guide 14. An optical image of the observation object is formed on a light receiving surface of the camera 15 by the rigid endoscope optical system 13. The camera 15 has, for example, a high resolution such as 4K resolution or 8K resolution. The image captured by the camera 15 is transmitted to a display device 17 as an image signal. The display device 17 displays the image captured by the camera 15.

Figure 2:
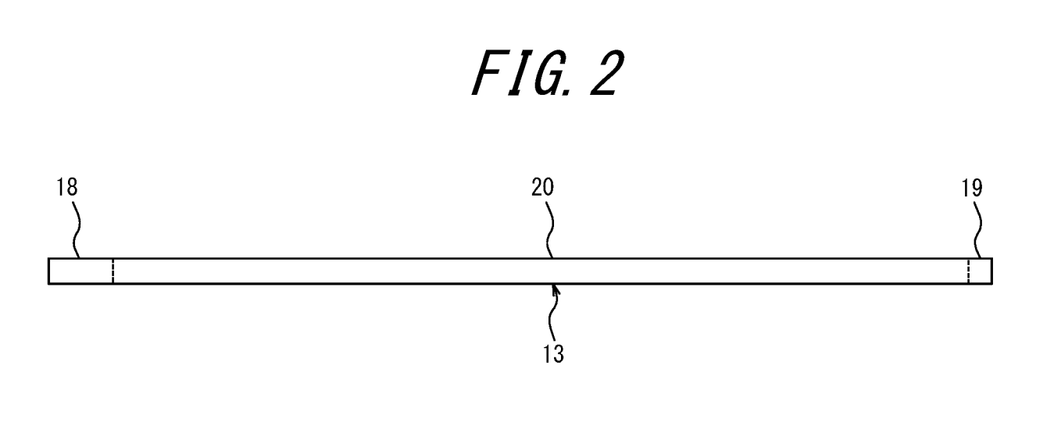
FIG. 2 is a schematic diagram illustrating a structure of a rigid endoscope optical system in FIG. 1.

The rigid endoscope optical system 13 will be described below. As illustrated in FIG. 2, the rigid endoscope optical system 13 includes an objective optical system 18, an imaging optical system 19, and a relay optical system 20. The objective optical system 18 is provided at the distal end of the insertion portion 11. The objective optical system 18 forms a real image of the observation object. The imaging optical system 19 forms the real image of the observation object on the light receiving surface of the camera 15. The relay optical system 20 is located between the objective optical system 18 and the imaging optical system 19. The relay optical system 20 transfers the real image of the observation object formed by the objective optical system 18, to the imaging optical system 19.

Figure 3:
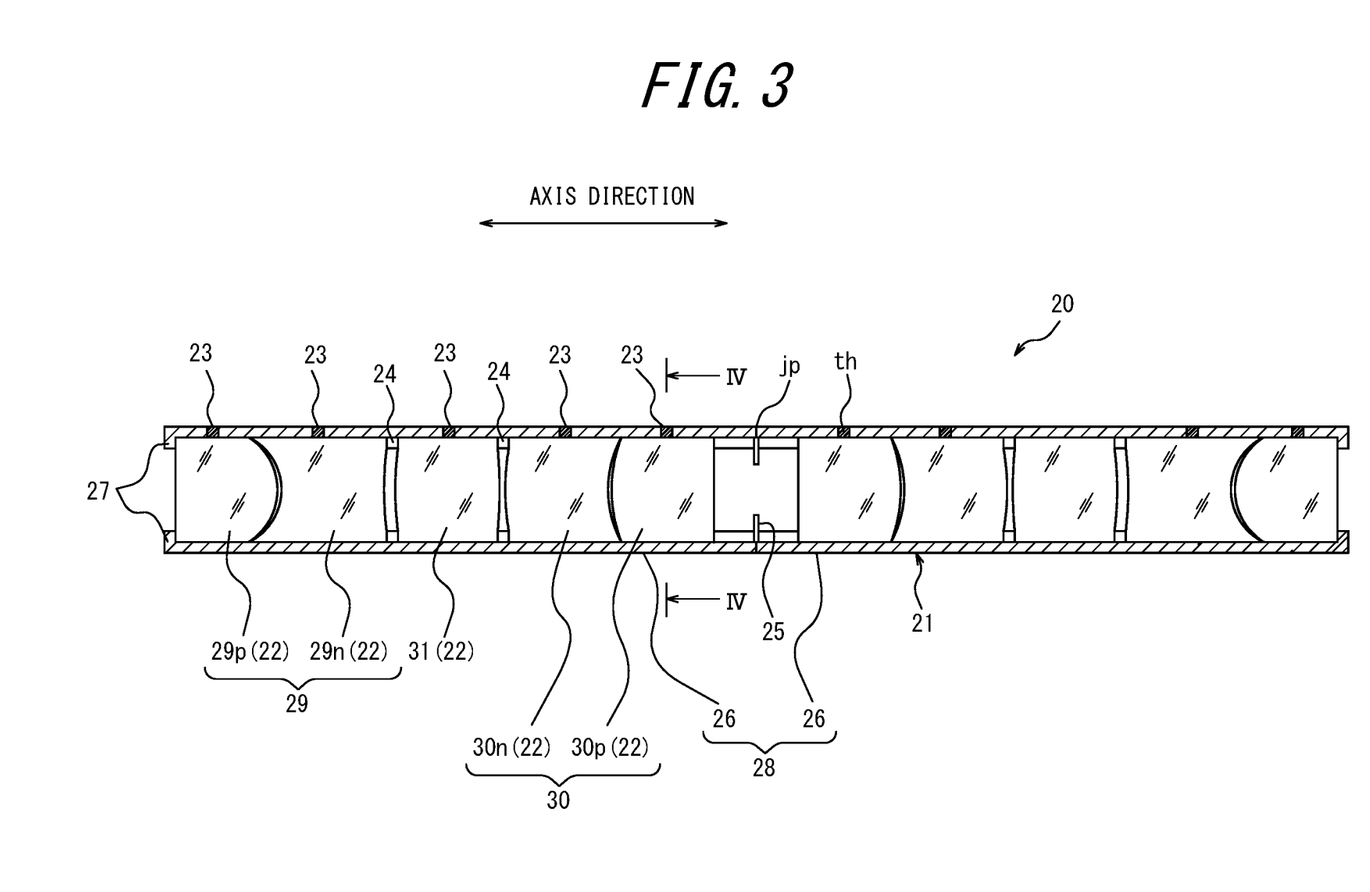
FIG. 3 is a sectional diagram of the relay optical system in FIG. 2 along an axis direction.

A structure of the relay optical system 20 will be described in detail below, with reference to FIG. 3. The relay optical system 20 includes a lens fixing frame 21 and a plurality of lenses 22. The relay optical system 20 may further include an adhesive body 23, a gap ring 24, and an aperture stop 25.

The lens fixing frame 21 has a plurality of tubular bodies 26. The tubular bodies 26 may be made of any material. For example, the tubular bodies 26 are made of metal such as brass, an aluminum alloy, or stainless steel. The plurality of tubular bodies 26 are joined coaxially to each other. The plurality of tubular bodies 26 may be joined by any method, such as welding.

In this embodiment, the plurality of tubular bodies 26 all have the same size and the same shape. An inner flange 27 is formed at one end of each tubular body 26 in the axis direction. Two tubular bodies 26 are joined at the end opposite to the end where the inner flange 27 is formed. The two tubular bodies 26 joined at the end opposite to the end where the inner flange 27 is formed form a connection tube 28. The lens fixing frame 21 includes at least one connection tube 28. The lens fixing frame 21 includes the number of connection tubes 28 corresponding to the length of the insertion portion 11. In a structure in which the lens fixing frame 21 includes a plurality of connection tubes 28, two connection tubes 28 are joined at their ends in the axis direction.

The plurality of lenses 22 may each be made of any glass material or any transparent resin. The plurality of lenses 22 are fixed in the lens fixing frame 21 so as to have a coincident optical axis. The plurality of lenses 22 are located at positions other than the joint position jp of the plurality of tubular bodies 26, in the axis direction of the lens fixing frame 21. The plurality of lenses 22 do not include a cemented lens. That is, the plurality of lenses 22 are not bonded to each other.

Lenses 22 included in a single connection tube 28 are designed so that a real image formed on one end surface of the single connection tube 28 will be formed on the other end surface of the single connection tube 28, and are fixed in the connection tube 28. Therefore, when the end surfaces of a plurality of connection tubes 28 are joined to each other, a real image can be transferred in the joined plurality of connection tubes 28 as a whole.

In this embodiment, part of the plurality of lenses 22 are provided in at least one of the plurality of tubular bodies 26 as a front lens group 29, a rear lens group 30, and a middle lens 31. In this embodiment, the same front lens group 29, the same rear lens group 30, and the same middle lens 31 are provided in each of the plurality of tubular bodies 26. The front lens group 29, the middle lens 31, and the rear lens group 30 convert each point image in a real image formed on the end surface of the tubular body 26 on the front lens group 29 side into a parallel light flux and emit it from the rear lens group 30.

The front lens group 29 is located at the end of the tubular body 26 where the inner flange 27 is formed. The front lens group 29 includes a lens 29$p$ having positive refractive power and a lens 29$n$ having negative refractive power arranged in this order from the side where the inner flange 27 is formed. The rear lens group 30 includes a lens 30$n$ having negative refractive power and a lens 30$p$ having positive refractive power arranged in this order from the side where the inner flange 27 is formed. The middle lens 31 is located between the front lens group 29 and the rear lens group 30. The middle lens 31 has positive refractive power.

In the front lens group 29, the lens 29$p$ having positive refractive power and the lens 29$n$ having negative refractive power may be butted against each other without being bonded, outside their effective diameter. The term "effective diameter" denotes a range that functions as a refractive surface of the lens, or a range in which a light beam passes in the plane of the lens in the state of the rigid endoscope optical system 13. In the rear lens group 30, the lens 30$p$ having positive refractive power and the lens 30$n$ having negative refractive power may be butted against each other without being bonded, outside their effective diameter.

Figure 4:
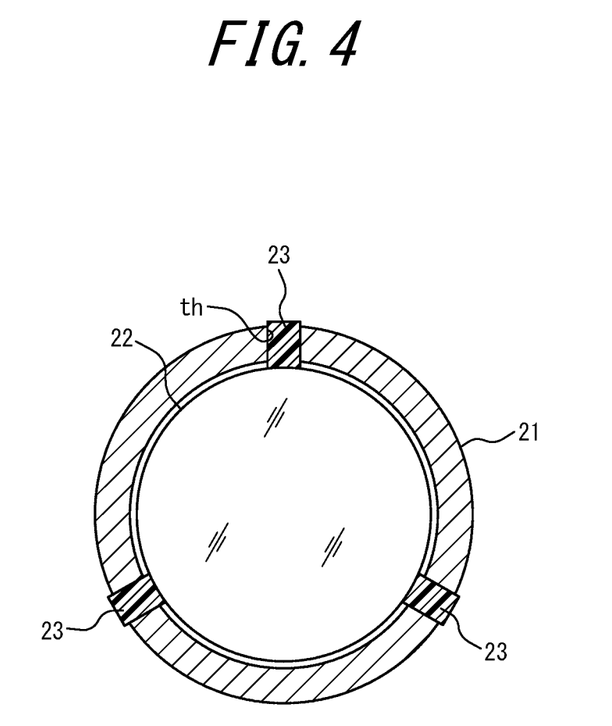
FIG. 4 is a sectional diagram of the relay optical system in FIG. 3 along line IV-IV.

The plurality of lenses 22 may be fixed to the lens fixing frame 21 by any mechanism. In this embodiment, the plurality of lenses 22 are fixed to the lens fixing frame 21 by the adhesive body 23. The adhesive body 23 extends from a through hole th formed on the cylindrical side wall of the lens fixing frame 21 to the outer edge of the lens 22. The through hole th is formed in each of at least three locations along the circumferential direction of the lens fixing frame 21, as illustrated in FIG. 4. The through holes th are preferably arranged equally in the circumferential direction. In a structure in which the through hole th is formed in each of three locations, the three through holes th are preferably arranged at intervals of 120°. In this embodiment, the through hole th is formed in each of three locations. Hence, in this embodiment, the adhesive body 23 fixes the lens 22 to the lens fixing frame 21 in three different locations along the circumferential direction of the lens 22.

The glass transition temperature of the adhesive body 23 may be higher than or equal to the sterilization temperature of the rigid endoscope 10 by the autoclave method. The sterilization temperature of the rigid endoscope 10 by the autoclave method is preferably 115° C. or higher, more preferably 130° C. or higher, and further preferably 140° C.

The gap ring 24 may be made of any material, but is preferably made of a material that satisfies Expression (1):

$$Ec \geq (El + Es) \quad (1).$$

In Expression (1), Ec is the thermal expansion coefficient of the lens fixing frame 21, El is the thermal expansion coefficient of each of the plurality of lenses 22, and Es is the thermal expansion coefficient of the gap ring 24. In this embodiment, the gap ring 24 is made of, for example, metal such as brass, an aluminum alloy, or stainless steel.

The gap ring 24 is located between the front lens group 29 and the middle lens 31 and between the middle lens 31 and the rear lens group 30. The gap ring 24 abuts the lens 22 outside the effective diameter. In the production of the relay optical system 20, the gap ring 24 adjusts the position of the lens 22 in the axis direction of the lens fixing frame 21 to align the lenses 22 in a desired position.

The aperture stop 25 is provided near the joint position jp of the tubular bodies 26. The aperture stop 25 adjusts the amount of light transferred by the relay optical system 20.

In the relay optical system 20 for the rigid endoscope 10 according to this embodiment having the above-described structure, the plurality of tubular bodies 26 are joined coaxially to each other to form the lens fixing frame 21. With such a structure, in the relay optical system 20, stress that occurs in the lens fixing frame 21 at high temperature and high pressure can be relaxed in the joined part. The relay optical system 20 can thus reduce the amount of misalignment of the lenses 22 at high temperature and high pressure. Consequently, the relay optical system 20 can reduce the decrease in initial optical property even when exposed to high temperature and high pressure. In a typical rigid endoscope, a lens fixing frame of a relay optical system is a single long cylinder. In a state in which many lenses are inserted in such a long cylinder with a gap ring being interposed between the lenses, the lenses are fixed by being sandwiched from both ends by flanges, caulking, pressing rings, or the like. When such a structure is exposed to high temperature, due to the differences in thermal expansion rate between the lens fixing frame, the lens, and the gap ring, for example, there is a possibility that the gap ring presses the lens harder than at normal temperature and as a result the surface of the lens distorts. Moreover, for example, there is a possibility that a gap forms between the gap ring and the lens and as a result the lens becomes displaced and misaligned. In the relay optical system 20 with the above-described structure, on the other hand, the lenses 22 can be fixed in each tubular body 26 that is shorter than the entire lens fixing frame 21, so that the lenses 22 can be positioned and aligned with high accuracy even by a fixing method other than pressing the lenses 22 from both ends with a gap ring being interposed therebetween. Therefore, the decrease in initial optical property when exposed to high temperature and high pressure can be reduced. Moreover, in the relay optical system 20, high-accuracy alignment in the optical axis direction can be achieved, and accordingly a cemented lens need not be used.

In the relay optical system 20 for the rigid endoscope 10 according to this embodiment, the plurality of lenses 22 in the relay optical system 20 do not include a cemented lens. A cemented lens is usually joined using an adhesive. Hence, the cemented lens can become cloudy as a result of being repeatedly exposed to a high-temperature environment. The cloudiness on the refractive surface of the cemented lens decreases the optical performance of the cemented lens such as transmittivity. The relay optical system 20 with the above-described structure, on the other hand, can suppress the decrease in optical performance caused by exposure to high temperature.

In the relay optical system 20 for the rigid endoscope 10 according to this embodiment, the lenses 22 are located at positions other than the joint position jp of the tubular bodies 26. At the joint position jp of the tubular bodies 26, high-accuracy lens alignment is difficult. Although high-accuracy alignment in the tubular body 26 can be performed by using a rod lens whose outer diameter is the same as the inner diameter of the tubular body 26 as part of the lenses, exposure to high temperature is likely to cause misalignment due to the difference in thermal expansion rate. In the relay optical system 20 with the above-described structure, on the other hand, the lenses 22 can be aligned with high accuracy without misalignment of the lenses 22.

In the relay optical system 20 for the rigid endoscope 10 according to this embodiment, the tubular body 26 has the front lens group 29 including the lens 29p having positive refractive power and the lens 29n having negative refractive power in proximity to each other, the rear lens group 30 including the lens 30n having negative refractive power and the lens 30p having positive refractive power in proximity to each other, and the middle lens 31 located between the front lens group 29 and the rear lens group 30. With such a structure, in the relay optical system 20, an incident light beam is refracted in the optical axis direction by the lens 29p having positive refractive power. Hence, in the relay optical system 20, a lens having a relatively small effective diameter with a relatively large NA can be used. Moreover, in the relay optical system 20, the lens 29n having negative refractive power in proximity to the lens 29p having positive refractive power can reduce chromatic aberration caused by the lens 29p having positive refractive power. In addition, in the relay optical system 20, the middle lens 31 having positive refractive index and adjacent to the lens 29n having negative refractive power can converge the light beam in the optical axis direction. Furthermore, in the relay optical system 20, the rear lens group 30 adjacent to the middle lens 31 can reduce chromatic aberration caused by the front lens group 29 and the middle lens 31. Since the rear lens group 30 includes the lens 30n having a negative refractive index and the lens 30p having a positive refractive index in the relay optical system 20, chromatic aberration can be further reduced.

In the relay optical system 20 for the rigid endoscope 10 according to this embodiment, in at least one of the front lens group 29 and the rear lens group 30, the lens 29p/30p having positive refractive power and the lens 29n/30n having negative refractive power are butted against each other outside their effective diameter. With such a structure, in the relay optical system 20, the lenses 22 can be fixed with a reduced number of gap rings 24 interposed between the lenses 22. Since the number of gap rings 24 that can cause misalignment due to the difference in thermal expansion rate is small in the relay optical system 20, the amount of misalignment of the lenses 22 can be further reduced.

In the relay optical system 20 for the rigid endoscope 10 according to this embodiment, the aperture stop 25 is provided near the joint position jp of the tubular bodies 26. In a structure in which the front lens group 29, the middle lens 31, and the rear lens group 30 convert each point image in a real image formed on the end surface of the tubular body 26 on the front lens group 29 side into a parallel light flux and emit it from the rear lens group 30 as mentioned above, displacement of the aperture stop 25 is less likely to cause degradation in resolution. Thus, the aperture stop 25 with a greater tolerance for displacement is provided near the joint position jp in the relay optical system 20, with it being possible to utilize the space effectively.

In the relay optical system 20 for the rigid endoscope 10 according to this embodiment, the adhesive body 23 extending from the through hole th formed in the lens fixing frame 21 to the outer edge of the lens 22 fixes the lens 22 to the lens fixing frame 21. With such a structure, in the relay optical system 20, the gap ring 24 is not used for fixing, so that the amount of displacement of each lens 22 with respect to the lens fixing frame 21 in the optical axis direction can be further reduced even when exposed to high temperature and high pressure. Moreover, in the relay optical system 20, each lens 22 can be aligned easily by adjusting the amount of the adhesive (the adhesive body 23 before curing) injected from the through holes th in three or more locations along the circumferential direction.

In the relay optical system 20 for the rigid endoscope 10 according to this embodiment, the glass transition temperature of the adhesive body 23 is higher than or equal to the sterilization treatment temperature. The adhesive body 23 may expand abnormally at the glass transition temperature or higher. With the foregoing structure, in the relay optical system 20, abnormal expansion of the adhesive body 23 can be prevented even when sterilization treatment by an autoclave is performed. Thus, in the relay optical system 20, misalignment or distortion of the lens 22 caused by abnormal expansion of the adhesive body 23 can be prevented.

In the relay optical system 20 for the rigid endoscope 10 according to this embodiment, the lens fixing frame 21, the plurality of lenses 22, and the gap ring 24 satisfying $Ec \geq (El+Es)$ are used. In the case where the thermal expansion of the lens fixing frame 21 is less than the thermal expansion of each lens 22 and the gap ring 24, stress from the gap ring 24 is applied to the surface of the lens 22, as a result of which displacement or distortion of the lens 22 can occur. With the foregoing structure, in the relay optical system 20, even when thermal expansion occurs when exposed to high temperature, the gap ring 24 is prevented from pressing the lens 22. Thus, in the relay optical system 20, displacement or distortion of the lens 22 can be prevented even when exposed to high temperature.

Although the presently disclosed techniques have been described by way of the drawings and embodiments, various changes and modifications may be easily made by those of ordinary skill in the art based on the present disclosure. Such various changes and modifications are therefore included in the scope of the present disclosure.

For example, although the rigid endoscope 10 enables viewing of the observation object using the camera 15 and the display device 17 in the foregoing embodiment, the observer may view the observation object from the proximal side of the rigid endoscope optical system 13 without using the camera 15. In this structure, an ocular optical system that forms a virtual image of a real image transferred by the relay optical system 20 is used in the rigid endoscope optical system 13 instead of the imaging optical system 19.

REFERENCE SIGNS LIST 10 rigid endoscope
11 insertion portion
12 operation portion
13 rigid endoscope optical system
14 light guide
15 camera
16 light source device
17 display device
18 objective optical system
19 imaging optical system
20 relay optical system
21 lens fixing frame
22 lens
23 adhesive body
24 gap ring
25 aperture stop
26 tubular body
27 inner flange
28 connection tube
29 front lens group
29$n$ lens having negative refractive power in front lens group
29$p$ lens having positive refractive power in front lens group
30 rear lens group
30$n$ lens having negative refractive power in rear lens group
30$p$ lens having positive refractive power in rear lens group
31 middle lens
jp joint position
th through hole

The invention claimed is:

1. A relay optical system for a rigid endoscope, comprising:
  a lens fixing frame having a plurality of tubular bodies that are joined coaxially to each other; and
  a plurality of lenses located in the lens fixing frame so as to have a coincident optical axis, at positions other than a joint position of the tubular bodies in an axis direction of the lens fixing frame, the plurality of lenses not including a cemented lens,
  wherein at least one of the plurality of tubular bodies has, as part of the plurality of lenses, a front lens group including a lens having positive refractive power and a lens having negative refractive power in proximity to each other, a rear lens group including a lens having negative refractive power and a lens having positive refractive power in proximity to each other, and a middle lens located between the front lens group and the rear lens group and having positive refractive power, and
  wherein in at least one of the front lens group and the rear lens group, the lens having positive refractive power and the lens having negative refractive power are butted against each other outside an effective diameter thereof.

2. The relay optical system for a rigid endoscope according to claim 1, further comprising
  an adhesive body extending from a through hole formed in each of at least three locations along a circumferential direction of the lens fixing frame to an outer edge of at least part of the plurality of lenses, and fixing the at least part of the plurality of lenses to the lens fixing frame.

3. A relay optical system for a rigid endoscope, comprising:
- a lens fixing frame having a plurality of tubular bodies that are joined coaxially to each other;
- a plurality of lenses located in the lens fixing frame so as to have a coincident optical axis, at positions other than a joint position of the tubular bodies in an axis direction of the lens fixing frame, the plurality of lenses not including a cemented lens; and
- an aperture stop for the plurality of lenses, the aperture stop being located near the joint position of the tubular bodies.

4. A relay optical system for a rigid endoscope, comprising:
- a lens fixing frame having a plurality of tubular bodies that are joined coaxially to each other;
- a plurality of lenses located in the lens fixing frame so as to have a coincident optical axis, at positions other than a joint position of the tubular bodies in an axis direction of the lens fixing frame, the plurality of lenses not including a cemented lens; and
- an adhesive body extending from a through hole formed in each of at least three locations along a circumferential direction of the lens fixing frame to an outer edge of at least part of the plurality of lenses, and fixing the at least part of the plurality of lenses to the lens fixing frame,
- wherein a glass transition temperature of the adhesive body is higher than or equal to a sterilization treatment temperature.

5. A relay optical system for a rigid endoscope, comprising:
- a lens fixing frame having a plurality of tubular bodies that are joined coaxially to each other; and
- a plurality of lenses located in the lens fixing frame so as to have a coincident optical axis, at positions other than a joint position of the tubular bodies in an axis direction of the lens fixing frame, the plurality of lenses not including a cemented lens,
- wherein $Ec \geq (El+Es)$, where $Ec$ is a thermal expansion coefficient of the lens fixing frame, $El$ is a thermal expansion coefficient of each of the plurality of lenses, and $Es$ is a thermal expansion coefficient of a gap ring that adjusts a position of at least part of the plurality of lenses in an optical axis direction.

* * * * *